United States Patent
Villari et al.

(10) Patent No.: US 10,478,061 B2
(45) Date of Patent: Nov. 19, 2019

(54) RETINOSCOPY PADDLE WITH INTEGRATED AXIS COMPASS OR ADAPTER, AND ASSOCIATED METHOD

(71) Applicant: GOOD-LITE CO., Elgin, IL (US)

(72) Inventors: Joseph Villari, Elgin, IL (US); Christian Greening, Pingree Grove, IL (US)

(73) Assignee: GOODLITE CO., Elgin, IL (US)

( * ) Notice: Subject to any disclaimer, the term of this patent is extended or adjusted under 35 U.S.C. 154(b) by 78 days.

(21) Appl. No.: 15/979,203

(22) Filed: May 14, 2018

(65) Prior Publication Data

US 2018/0325372 A1   Nov. 15, 2018

Related U.S. Application Data

(63) Continuation of application No. 14/990,875, filed on Jan. 8, 2016, now abandoned.

(60) Provisional application No. 62/101,599, filed on Jan. 9, 2015.

(51) Int. Cl.
*B43L 9/04* (2006.01)
*A61B 3/103* (2006.01)

(52) U.S. Cl.
CPC .................................. *A61B 3/1035* (2013.01)

(58) Field of Classification Search
CPC .......... B43L 13/001; B43L 9/02; B43L 9/025
USPC ........ 351/204, 200; 33/27.02, 27.03, 27.032, 33/27.033
See application file for complete search history.

(56) References Cited

U.S. PATENT DOCUMENTS

| 6,405,553 | B1 | 6/2002 | Thorn et al. |
| 6,457,247 | B1* | 10/2002 | Lin ........................ G01B 3/563 33/1 N |
| 7,383,635 | B1 | 6/2008 | Stoneberg |

OTHER PUBLICATIONS http://www.eyecareandcure.com/ECC-Products/Retinoscopy/School-bus-Retinoscopy-Racks, Eyecare and Cure, printed on Jan. 8, 2016.

* cited by examiner

*Primary Examiner* — Hung X Dang
(74) *Attorney, Agent, or Firm* — Fay Sharpe LLP

(57) ABSTRACT

An improved retinoscopy paddle with lens received through openings extending through the paddle member has an axis compass with indicia for assessing the range of refraction error and axis of astigmatism in the eyes of a patient as part of an optical examination. The axis compass may be formed on the paddle member or on a receptacle member adapted for operative receipt on as associated retinoscopy paddle. A method is provided for integrating a retinoscopy paddle and axis compass.

20 Claims, 2 Drawing Sheets

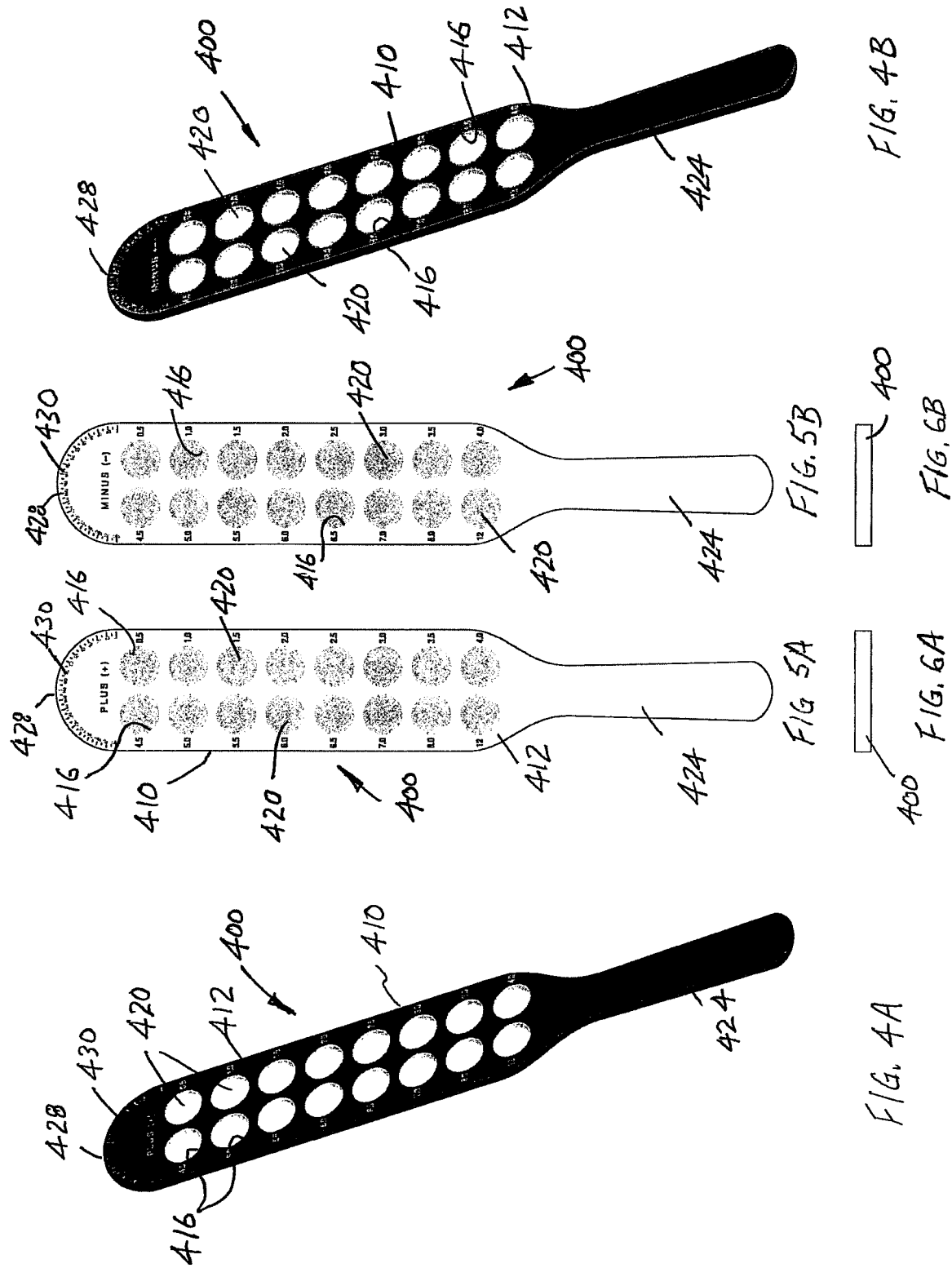

RETINOSCOPY PADDLE WITH INTEGRATED AXIS COMPASS OR ADAPTER, AND ASSOCIATED METHOD

This application claims the priority benefit of US application Ser. No. 14/990,875, filed Jan. 8, 2016, now abandoned, which claims the priority benefit of U.S. Provisional Application No. 62/101,599, filed Jan. 9, 2015, the entire disclosures of which are expressly incorporated herein by reference.

BACKGROUND

The present disclosure relates to the art of measuring objective refraction, and, more particularly, to a retinoscopy rack or paddle, axis compass, and method of integrating or adapting same.

In known arrangements, a retinoscopy rack or paddle (or sometimes referred to as a "ret rack") is used with a retinoscope for example by an associated eye-care practitioner such as an optometrist or ophthalmologist (sometimes referred hereinafter as "professional") to assess a range of refraction error and also to assess a limited axis of astigmatism in the eyes of a patient as part of an optical examination. A beam of light is passed from the retinoscope through one of the lenses in a retinoscopy paddle into the eye of a patient while the patient views a distant object, allowing the professional to examine how light is reflected off the retina of the patient. The error of refraction can be determined by using a retinoscopy paddle that includes or holds a series of lenses typically in an ordered fashion, that is the lenses of different strength are preferably arranged in the paddle in a progressive or orderly fashion to aid the professional in positioning a particular lens over the eye of the patient, and then quickly and easily positioning a different lens of a different optical strength over the eye. The professional can evaluate the patient by alternately and selectively directing light through one of the lenses, and then viewing through a lens of a different optical strength, e.g., greater or lesser degree of optical strength, until the retinal reflex is observed as being in a desired or normal range through the retinoscope.

Existing retinoscopy paddles lack the ability to measure oblique astigmatism angles, that is, existing retinoscopy paddles are generally limited to measuring the axis of astigmatism at angles of 90 and 180 degrees exclusively. With existing retinoscopy paddles, the associated professional must hold the retinoscopy paddle at an angle to determine the best acuity setting for the patient, but lacks a quick, convenient, accurate, and efficient method of also measuring the astigmatism angle. When using an existing retinoscopy paddle, the associated user must use a separate, second device, such as a phoropter, to attempt to replicate the angle. This method can become burdensome and time consuming for the associated professional.

It is desirable to provide a retinoscopy paddle that neither compromises the highest quality of measurement with expediency and nor is as time consuming, burdensome, or inefficient as using existing retinoscopy paddles and a separate device to evaluate or measure oblique astigmatism angles.

SUMMARY

The present disclosure provides an integrated retinoscopy rack or paddle with an integrated or attachable axis compass for use by an eye-care practitioner or professional.

The disclosure provides an associated user a quick, accurate, efficient, and convenient means of measuring the astigmatism angle of the patient without the need to use multiple devices.

The disclosure allows the practitioner/professional to explain and demonstrate based on experience with the patient's vision complaints, and offer a solution to reduce or eliminate the problem.

The retinoscopy paddle includes an elongated paddle member having opposing front and rear surfaces and at least one opening and preferably a number of openings extending through the paddle member. The openings extend from the front to rear surface of the paddle member. The paddle member further includes at least one lens received in the paddle member, i.e., one lens in each opening where the lenses are and an axis compass including indicia thereon. The axis compass is disposed adjacent a first end of the paddle member.

An axis compass adapted for operative receipt on an associated retinoscopy paddle in accordance with the present novel concept is provided that includes opposing front and rear surfaces and opposing first and second ends. At least the front surface includes indicia thereon and the second end of the axis compass is configured for selective attachment to an associated retinoscopy paddle.

A method in accordance with the present novel concept is provided that includes providing an axis compass, providing a retinoscopy paddle, and integrating the axis compass with the retinoscopy paddle.

Other and further objects of the present novel concept will become apparent to those skilled in the art upon a study of the following specification, appended claims and accompanying drawings.

BRIEF DESCRIPTION OF THE DRAWINGS

FIG. 4A is a perspective view of one embodiment of a plus retinoscopy paddle integrated with an axis compass according to the present novel concept.

FIG. 4B is a perspective view of one embodiment of a minus retinoscopy paddle integrated with an axis compass according to the present novel concept.

FIG. 5A is a front view of the retinoscopy paddle shown in FIG. 4A.

FIG. 5B is a front view of the retinoscopy paddle shown in FIG. 4B.

FIG. 6A is a top view of the retinoscopy paddle shown in FIG. 4A.

FIG. 6B is a top view of the retinoscopy paddle shown in FIG. 4B.

DETAILED DESCRIPTION

Figure 1A:
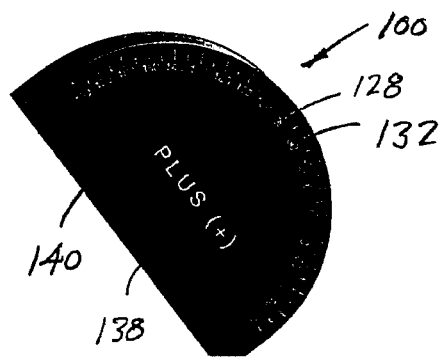
FIG. 1A is a perspective view of one embodiment of a plus axis compass according to the present novel concept.
Figure 1B:
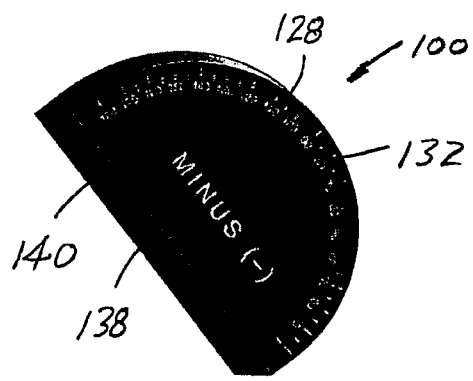
FIG. 1B is a perspective view of one embodiment of a minus axis compass according to the present novel concept.

Referring now in greater detail to the drawings, wherein the showings are for the purposes of illustrating exemplary embodiments of the subject novel concept only, and not for the purpose of limiting the same, FIGS. 1A and 1B illustrate an axis compass 100 adapted for operative receipt of an associated retinoscopy paddle. Axis compass 100 includes a front surface 112 opposite a rear surface. Front surface 112 includes indicia 132. Indicia 132 may be formed directly on front surface 112 of axis compass 100. Alternatively, indicia 132 may be painted, embossed, drawn, carved, or otherwise formed on front surface 112 of axis compass 100 by any means presently known in the art. Axis compass 100 further includes a first end 128 opposite a second end 138. Second end 138 is configured for selective attachment to an associated retinoscopy paddle. In the embodiment shown in FIGS. 1A and 1B, second end 138 of axis compass 100 includes female receptacle 140 dimensioned to matingly receive an end of an associated retinoscopy paddle. Another means of integrating axis compass 100 with an associated retinoscopy paddle can be achieved by securing the retinoscopy paddle to the axis compass using a retainer clip. Second end 138 may be integrated with a retinoscopy paddle via any means presently known in the art. The result of integrating axis compass 100 with a retinoscopy paddle is that the associated user need only use one device to measure the range of refraction error and axis of astigmatism, which cannot be achieved using existing retinoscopy paddles. Axis compass 100 offers the associated user a quick, accurate, efficient, and convenient means of measuring the astigmatism angle of the patient without the need to use multiple devices. In the embodiment shown in FIGS. 1A and 1B, both front surface 112 and the rear surface of axis compass 100 are semicircularly shaped. In the embodiment shown in FIGS. 1A and 1B, indicia 132 includes marks approximately every 5 degrees from approximately 0 to 180 degrees for measuring the astigmatism angle of a patient quickly and accurately. The rear surface of axis compass 100 may also include indicia.

Figure 2A:
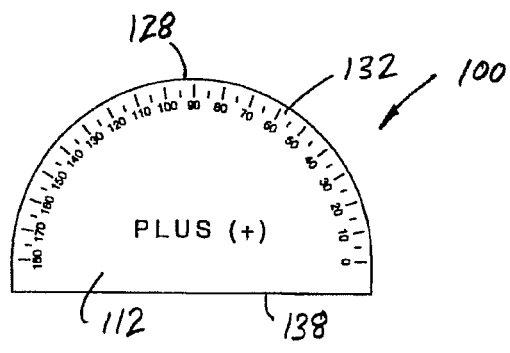
FIG. 2A is a top view of the axis compass shown in FIG. 1A.
Figure 2B:
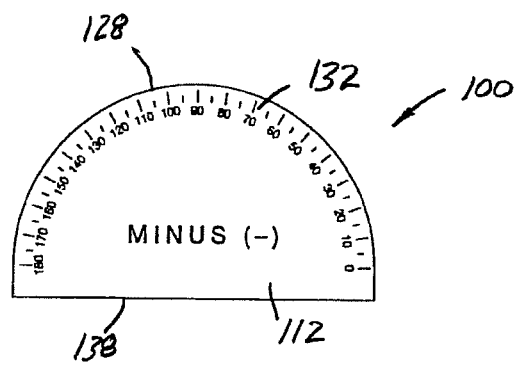
FIG. 2B is a top view of the axis compass shown in FIG. 1B.

FIGS. 2A and 2B show second end 138 of axis compass 100. Second end 138 is configured for selective attachment to an associated retinoscopy paddle. In the embodiment shown in FIGS. 2A and 2B, second end 138 of axis compass 100 includes female receptacle 140 dimensioned to matingly receive an end of an associated retinoscopy paddle. Another means of integrating axis compass 100 with an associated retinoscopy paddle can be achieved by securing the retinoscopy paddle to the axis compass using a retainer clip. Second end 138 may be integrated with a retinoscopy paddle via any means presently known in the art.

Figure 3A:
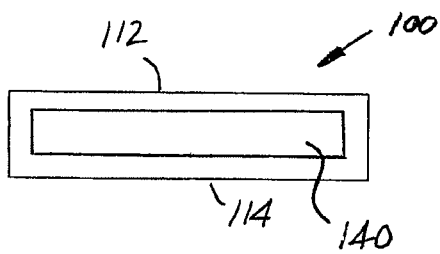
FIG. 3A is a front view of the axis compass shown in FIG. 1A.
Figure 3B:
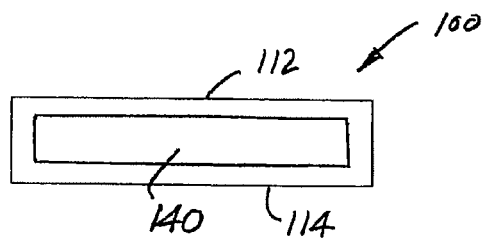
FIG. 3B is a front view of the axis compass shown in FIG. 1B.

FIGS. 3A and 3B show front surface 112 of axis compass 100. Front surface 112 includes indicia 132. Indicia 132 may be formed directly on front surface 112 of axis compass 100, or indicia 132 may be painted, embossed, drawn, carved, or otherwise formed on front surface 112 of axis compass 100 by any means presently known in the art. In the embodiment shown in FIGS. 3A and 3B, indicia 132 includes marks approximately every 5 degrees from approximately 0 to 180 degrees for measuring the astigmatism angle of a patient quickly and accurately. In the embodiment shown in FIGS. 1A and 1B, both front surface 112 and the rear surface of axis compass 100 are semicircularly shaped.

FIGS. 4A and 4B illustrate a retinoscopy paddle 400. Retinoscopy paddle 400 includes an elongated paddle member 410 having a front surface 412 opposite a rear surface. At least one opening 416 extends through paddle member 410 from front surface 412 to the rear surface. Paddle member 410 further includes at least one lens 420 received in paddle member 410. In the embodiment shown in FIGS. 4A and 4B, paddle member 410 includes a plurality of lenses 420 each received in corresponding openings 416 in paddle member 410. In the embodiment shown in FIGS. 4A and 4B, the lenses 420 are plus or minus lenses approximately 16 mm in diameter, glass, and recessed within paddle member 410 relative to at least one of front surface 412 and the rear surface of paddle member 410. Paddle member 410 further includes axis compass 430 disposed adjacent first end 428 of paddle member 410. It is to be understood that while axis compass 100 in FIGS. 1A and 1B is a separate member adapted for operative receipt on an associated retinoscopy paddle, axis compass 430 is not a separate member from retinoscopy paddle 400. Axis compass 430 includes indicia 432 on at one of least front surface 412 or the rear surface of paddle member 410. Indicia 432 may be formed directly on front surface 412 of paddle member 410. Alternatively, indicia 432 may be painted, embossed, drawn, carved, or otherwise formed on front surface 412 of paddle member 410 by any means presently known in the art. In the embodiment shown in FIGS. 4A and 4B, paddle member 410 further includes handle 424 longitudinally opposite first end 428. Handle 424 is configured to be gripped by a hand of an associated user. Axis compass 430 may be formed on a receptacle member configured to operatively engage first end 428 of paddle member 410. The receptacle member may include a slot dimensioned for receipt over at least a portion of first end 428 of paddle member 410. Indicia 432 may be formed directly on the receptacle member. The receptacle member may be integrated with a retinoscopy paddle via any means presently known in the art.

FIGS. 5A and 5B show front surface 412 of retinoscopy paddle 400. Front surface 412 is opposite the rear surface of paddle member 410. At least one of front surface 412 and the rear surface of paddle member 410 includes indicia 432. Indicia 432 may be formed directly on front surface 412. Alternatively, indicia 432 may be painted, embossed, drawn, carved, or otherwise formed on front surface 412 by any means presently known in the art. At least one opening 416 extends through paddle member 410 from front surface 412 to the read surface.

FIGS. 6A and 6B show first end 428 of retinoscopy paddle 400. Handle 424 is longitudinally opposite first end 428 of retinoscopy paddle 400.

By way of example, and not limitation, an axis compass may be integrated with a retinoscopy paddle by sliding a first end of the retinoscopy paddle into a mating recess of the axis compass. The integration of the axis compass and retinoscopy paddle could alternatively be performed by securing the retinoscopy paddle to the axis compass using a retainer clip. The axis compass may be integrated with the retinoscopy paddle via any means presently known in the art.

While the subject novel concept has been described with reference to the foregoing embodiments and considerable emphasis has been placed herein on the structures and structural interrelationships between the component parts of the embodiments disclosed, it will be appreciated that other embodiments can be made and that many changes can be made in the embodiments illustrated and described without departing from the principles of the subject novel concept. Obviously, modifications and alterations will occur to others upon reading and understanding the preceding detailed description. Accordingly, it is to be distinctly understood that the foregoing descriptive matter is to be interpreted merely as illustrative of the present novel concept and not as a limitation. As such, it is intended that the subject novel concept be construed as including all such modifications and alterations insofar as they come within the scope of the appended claims and any equivalents thereof.

What is claimed is:

1. A retinoscopy paddle comprising:
   an elongated paddle member having
      a front surface opposite a rear surface;
      plural openings extending through the paddle member from the front surface to the rear surface;
      plural lenses received in the paddle member in respective, corresponding openings; and
      an axis compass disposed adjacent a first end of the paddle member and including indicia on at least one of the front and rear surfaces of the paddle member.

2. The retinoscopy paddle of claim 1 further comprising a handle configured to be gripped by a hand of an associated user.

3. The retinoscopy paddle of claim 2 wherein the axis compass indicia are formed directly on the paddle member.

4. The retinoscopy paddle of claim 1 wherein the axis compass indicia are formed on the paddle member.

5. The retinoscopy paddle of claim 1 wherein the axis compass indicia are formed on both the front and rear surfaces of the paddle member.

6. The retinoscopy paddle of claim 1 wherein the axis compass is formed on a receptacle member configured to operatively engage the first end of the paddle member.

7. The retinoscopy paddle of claim 6 wherein the receptacle member includes a slot dimensioned for receipt over at least a portion of the first end of the paddle member.

8. The retinoscopy paddle of claim 1 wherein the axis compass further includes at least one retainer clip for securing the axis compass to the first end of the paddle member.

9. The retinoscopy paddle of claim 1 further comprising a handle configured for gripping by a hand of an associated user, wherein the handle is longitudinally opposite the first end.

10. The retinoscopy paddle of claim 1 wherein the axis compass is formed directly on the receptacle member.

11. The retinoscopy paddle of claim 1 wherein the indicia include marks approximately every 5 degrees from approximately 0 to 180 degrees.

12. The retinoscopy paddle of claim 1 wherein each of the plural lenses is approximately 16 mm in diameter.

13. The retinoscopy paddle of claim 1 wherein each of the plural lenses is glass.

14. The retinoscopy paddle of claim 1 wherein the plural lenses are recessed within the paddle member relative to at least one of the front and rear surfaces.

15. The retinoscopy paddle of claim 1 wherein the plural lenses are either a plus or minus lens.

16. A method of forming a retinoscopy paddle comprising:
   providing an elongated paddle member having a front surface opposite a rear surface;
   providing plural openings extending through the paddle member from the front surface to the rear surface;
   receiving plural lenses in the paddle member in respective openings; and
   integrating an axis compass disposed adjacent a first end of the paddle member and including indicia on at least one of the front and rear surfaces of the paddle member.

17. The method of claim 16 wherein the step of integrating includes sliding a first end of the retinoscopy paddle into a mating recess of the axis compass.

18. The method of claim 17 further comprising dimensioning a slot on the receptacle member for receipt over at least a portion of the first end of the paddle member.

19. The method of claim 16 wherein the step of integrating includes forming the axis compass indicia directly on the paddle member.

20. The method of claim 16 wherein the step of integrating includes forming the axis compass indicia directly on both the front and rear surfaces of the paddle member.

* * * * *